(12) United States Patent
Bretz (10) Patent No.: US 10,285,929 B1
(45) Date of Patent: May 14, 2019

(54) COMPOSITION FOR PROMOTING ORAL AND GENERAL HEALTH AND METHOD FOR FORMING AND USING THE SAME

(71) Applicant: PITTS AND BRETZ DEVELOPMENT PARTNERS, Nevada City, CA (US)

(72) Inventor: Walter A. Bretz, Nevada City, CA (US)

(73) Assignee: PITTS AND BRETZ DEVELOPMENT PARTNERS, Nevada City, CA (US)

( * ) Notice: Subject to any disclaimer, the term of this patent is extended or adjusted under 35 U.S.C. 154(b) by 0 days.

(21) Appl. No.: 15/901,197

(22) Filed: Feb. 21, 2018

(51) Int. Cl.
*A61K 8/20* (2006.01)
*A61K 8/96* (2006.01)
*A61Q 11/00* (2006.01)

(52) U.S. Cl.
CPC .................. *A61K 8/96* (2013.01); *A61K 8/20* (2013.01); *A61Q 11/00* (2013.01)

(58) Field of Classification Search
None
See application file for complete search history.

(56) References Cited

U.S. PATENT DOCUMENTS

2009/0092565 A1* 4/2009 Koyama .................. A23G 4/06
424/57

* cited by examiner

*Primary Examiner* — Nannette Holloman
(74) *Attorney, Agent, or Firm* — Hoffman Warnick LLC (57) ABSTRACT

A composition for inhibiting enamel demineralization, promoting enamel remineralization and/or increasing salivary secretory immunoglobulin A is disclosed. The composition may contain lithothamnium calcareum (LC). The composition may comprise a first solution comprising at least 0.01% by weight LC and a second solution comprising an amount of hydrochloric acid (HCL) sufficient to adjust the pH of the composition to a physiological pH. A method of inhibiting enamel demineralization and promoting enamel remineralization is also disclosed. The method may include exposing a tooth to a LC containing composition. The method may further include both topically and systemically exposing the tooth to an LC containing composition. A method of increasing salivary secretory Immunoglobulin A (SIgA) in a mammal is also disclosed. The method may include topically exposing an oral cavity to a LC containing composition. The method may further include topically and systemically exposing the oral cavity to an LC containing composition.

20 Claims, 9 Drawing Sheets

| ANALYTE | UNITS | L. calcareum | ANALYTE | UNITS | L. calcareum |
|---|---|---|---|---|---|
| Aluminum | ppm | 1420 | Mercury | ppm | 0.011 |
| Antimony | ppm | 4.57 | Molybdenum | ppm | <0.1 |
| Arsenic | ppm | 0.11 | Neodymium | ppm | 3.51 |
| Barium | ppm | 5.37 | Nickel | ppm | 0.074 |
| Beryllium | ppm | 0.081 | Niobium | ppm | <0.1 |
| Bismuth | ppm | 2.19 | Osmium | ppm | <0.05 |
| Boron | ppm | 12.1 | Palladium | ppm | <0.05 |
| Bromine | ppm | 11.5 | Phosphorus | ppm | 169. |
| Cadmium | ppm | <0.03 | Platinum | ppm | <0.05 |
| Calcium | ppm | 279,000 | Potassium | ppm | 427. |
| Carbon | ppm | 124,000 | Praseodymium | ppm | 0.63 |
| Cerium | ppm | 2.11 | Rhenium | ppm | <0.2 |
| Cesium | ppm | 2.66 | Rhodium | ppm | <0.05 |
| Chloride | ppm | 2370. | Rubidium | ppm | 27.6 |
| Chromium | ppm | 5.10 | Ruthenium | ppm | 0.055 |
| Cobalt | ppm | 0.107 | Samarium | ppm | 0.67 |
| Copper | ppm | 1.59 | Scandium | ppm | 0.685 |
| Dysprosium | ppm | 1.15 | Selenium | ppm | 0.060 |
| Erbium | ppm | 18.9 | Silica | ppm | 28,000 |
| Europium | ppm | <0.1 | Silver | ppm | 1.78 |
| Fluoride | ppm | 7.55 | Sodium | ppm | 3970. |
| Gadolinium | ppm | 3.04 | Strontium | ppm | 2190. |
| Gallium | ppm | 1.27 | Sulfur | ppm | 940. |
| Germanium | ppm | 3.08 | Tantalum | ppm | <0.05 |
| Gold | ppm | <0.05 | Tellurium | ppm | 0.066 |
| Hafnium | ppm | <0.1 | Terbium | ppm | <0.2 |
| Holmium | ppm | <0.1 | Thallium | ppm | 0.33 |
| Indium | ppm | 0.17 | Thorium | ppm | 0.081 |
| Iodine | ppm | 10.6 | Thulium | ppm | <0.05 |
| Iridium | ppm | <0.05 | Tin | ppm | 0.197 |
| Iron | ppm | 10,100. | Titanium | ppm | 31.1 |
| Lanthanum | ppm | 0.314 | Tungsten | ppm | <0.05 |
| Lead | ppm | 0.061 | Vanadium | ppm | 12.9 |
| Lithium | ppm | 3.90 | Ytterbium | ppm | 0.237 |
| Lutetium | ppm | 0.310 | Yttrium | ppm | 1.74 |
| Magnesium | ppm | 99,800 | Zinc | ppm | 16.2 |
| Manganese | ppm | 90.5 | Zirconium | ppm | 0.642 |

FIG. 1

|  | Concentration (mg/L) | | | |
| --- | --- | --- | --- | --- |
|  | Ca | P | Mg | F |
| 0.01% LC | 4.7 ± 0.01 | Less than detectable | 0.41 ± 0.01 | Less than detectable |
| 0.03% LC | 13.5 ± 0.02 | Less than detectable | 1.01 ± 0.005 | Less than detectable |

FIG. 2

|  | Intact Enamel Knopps Hardness (KHN) | | |
| --- | --- | --- | --- |
|  | Pre-Treatment | Post-Treatment | % Difference |
| Negative Control (Distilled Water) | 351.1 ± 22.0 | 249.2 ± 19.3 | -29.0 ± 14.9 |
| Positive Control (0.05% NaF) | 367.0 ± 18.3 | 301.0 ± 27.7 | -17.6 ± 11.6 |
| 0.01% LC | 372.5 ± 16.8 | 311.5 ± 25.6 | -16.4 ± 6.7 |
| 0.03% LC | 388.6 ± 11.4 | 338.9 ± 19.5 | -12.8 ± 7.2 |

FIG. 3

| | Carious Induced Enamel Knopps Hardness (KHN) | | | |
|---|---|---|---|---|
| | Pre-Treatment | Post-Lesion Induction | Post-Treatment | % Difference |
| Negative Control (Distilled Water) | 351.7 ± 19.5 | 95.2 ± 23.4 | 78.5 ± 20.5 | -6.5 ± 5.52 |
| Positive Control (0.05% NaF) | 348.0 ± 24.3 | 94.0 ± 25.3 | 103.0 ± 21.3 | 14.5 ± 9.15 |
| 0.01% LC | 374.5 ± 25.1 | 72.5 ± 21.5 | 96.5 ± 17.1 | 12.1 ± 8.33 |
| 0.03% LC | 362.2 ± 20.4 | 91.3 ± 27.8 | 118.1 ± 19.2 | 26.15 ± 10.25 |

|  | Carious Induced Enamel Knopps Hardness (KHN) | | | |
| --- | --- | --- | --- | --- |
|  | Pre-Treatment | Post-Lesion Induction | Post-Treatment | % Difference |
| Positive Control (0.05% NaF) | 335.0 ± 18.4 | 93.5 ± 8.2 | 123.0 ± 10.3 | 12.3 ± 9.4 |
| 0.03% LC | 342.3 ± 20.1 | 91.3 ± 10.8 | 185.7 ± 16.5 | 37.6 ± 14.6 |

FIG. 9

|  | Carious Induced Enamel Knopps Hardness (KHN) | | | |
| --- | --- | --- | --- | --- |
|  | Pre-Treatment | Post-Lesion Induction | Post-Treatment | % Difference |
| Negative Control (Distilled Water) | 349.1 ± 17.5 | 98.2 ± 10.6 | 107.5 ± 8.1 | 3.7 ± 3.1 |
| 0.03% LC | 347.6 ± 19.5 | 94.1 ± 12.1 | 181.2 ± 15.3 | 34.3 ± 9.8 |

FIG. 10

|  | 0.03% LC & 500mg LC Capsule (n=85) | 0.03% LC (n=69) | p= |
|---|---|---|---|
| White Spot (V1) |  |  |  |
| Mean (SD) | 6.3 (3.9) | 6.9 (4.2) | 0.3197[#] |
| Median (Q1 – Q3)[‡] | 5 (3 – 8) | 6 (4 – 8) | 0.2838[§] |
| White Spot (V2) |  |  |  |
| Mean (SD) | 3.5 (2.1) | 3.2 (2.5) | 0.3893[#] |
| Median ((Q1 – Q3)[‡] | 3 (2 – 5) | 3 (1 – 4) | 0.3129[§] |
| WS Difference (V2 – V1) |  |  |  |
| Mean (SD) | -2.7 (2.9) | - 3.7 (3.6) | 0.0665[#] |
| Median ((Q1 – Q3)[‡] | -2 (-4 - 0) | -3 (-5 - -1) | 0.0783[§] |

[†]SD = Standard Deviation; [‡]Q1 = First Quartile and Q3 = Third quartile ; [#]p-value for a t-test; [§]value for Wilcoxson rank test; WS-white spot

FIG. 11

|  | 0.03% LC & 500mg LC Capsule (n=44) | 0.03% LC (n=42) | p= |
|---|---|---|---|
| Sex |  |  |  |
| Male | 23 (52.3) | 21 (50.0) | 0.8340[*] |
| Female | 21 (47.7) | 21 (50.0) |  |
| Age |  |  |  |
| (Mean ± SD) | 9.4 (1.5) | 9.2 (1.7) | 0.6324[#] |
| Pre-Treatment SIgA Concentration (µg/min) Median values (Q1 – Q3)[‡] | 33.2 (24.3 – 51.1) | 38.7 (30.4 – 56.1) | 0.1652[§] |
| Post-Treatment SIgA Concentration (µg/min) Median values (Q1 – Q3)[‡] | 53.6 (37.8 – 93.8) | 44.2 (32.4 – 53.5) | 0.0264[§] |
| 6 Months Post-Treatment SIgA Concentration (µg/min) Median values (Q1 – Q3)[‡] | 65.3 (37.7 – 99.5) | 44.1 (31.1-61.0) | 0.1705 |

[*] p-value for chi-square; [#]p-value for a t-test; [§]value for Wilcoxson rank test.
[‡]Q1 = First Quartile and Q3 = Third quartile

FIG. 12

|  | 0.03% LC & 500mg LC Capsule VS. 0.03% LC (Pre-Age Control) | 0.03% LC & 500mg LC Capsule VS. 0.03% LC (Post-Age Control) |
|---|---|---|
| Increase in SIgA from Pre-Treatment to 6 months Post-Treatment (%) | 32.12 | 11.23 |
| p= | 0.0520 | 0.4886 |

FIG. 13

ND METHOD
COMPOSITION FOR PROMOTING ORAL AND GENERAL HEALTH AND METHOD FOR FORMING AND USING THE SAME

BACKGROUND

The present disclosure relates to promoting oral and general health, and more specifically, to inhibiting demineralization, promoting remineralization and increasing salivary secretory immunoglobulin A (SIgA) using lithothamnium calcareum (LC) containing compositions.

Demineralization is the process of removing mineral ions from hydroxyapatite (HA) crystals of hard tissues such as bone, dentin, enamel, etc. Enamel is a highly mineralized hard tissue that shelters mammalian teeth from physical, chemical and biological injuring sources. Throughout the life of a mammal, enamel is particularly at risk of demineralization due to the anatomical location of the teeth and the resulting exposure to demineralization inducing environments. For example, mammalian teeth are constantly exposed to acidic foods, beverages, microbiota of the oral cavity, oral health products, etc.

The demineralization of enamel is known to cause a host of problems, including but not limited to carious and erosion lesions. For example, carious lesions may develop as a consequence of an interplay of factors, wherein over time, the presence of a distinct microbiome in biofilms and high frequency of disaccharides intake and hydrolysis (e.g., sucrose) disrupt the homeostatic concentration of calcium and phosphate between enamel and oral fluids (i.e., whole saliva and biofilm fluid). Erosion lesions on the other hand may be caused by repeated exposure of teeth to acid from either exogenous sources (e.g., acidic food, beverages, drugs, oral health products, etc.) or endogenous sources (e.g., gastric juice). Carious and erosion lesions, both a result of demineralization, may cause tooth pain and discomfort among other health problems if left untreated.

Due to these and other problems associated with the demineralization of enamel, the inhibition of enamel demineralization has become an important topic for dental clinicians and scientists. Demineralization is reversible through a process referred to as remineralization. Specifically, partially demineralized HA crystals of tooth enamel can regrow to their original size if exposed to proper conditions for remineralization. Therefore, remineralization has also become a popular topic for treating demineralized enamel.

Conventional treatments for inhibiting and treating demineralization include a variety of fluoride based products. For example, professional application of systemic or local (topical) fluoride enhances mineral uptake by enamel, which in turn inhibits enamel demineralization. Further, additional compounds, such as arginine and other calcium and/or phosphate compounds are conventionally added to the fluoride products to ensure a sufficient amount of calcium and/or phosphate and proper pH levels to promote enamel remineralization.

One challenge associated with fluoride based treatments includes environmental health hazards associated with high doses of fluoride uptake. For example, acute or chronic exposure to high doses of fluoride can result in dental and skeletal fluorosis. Dental fluorosis may be characterized by hypermineralization of enamel due to subsurface porosity below a well-mineralized region. Dental fluorosis may result in enamel discoloration and physical damage to teeth. Another challenge associated with fluoride based treatments includes leveling off of its effectiveness over time. For example, while a rapid decrease in carious lesions associated with increased fluoride use was observed in the 1970s, it has since leveled off, reaching a plateau in the 1990s. Yet another challenge associated with fluoride based products includes the limited availability for a variety of low resource demographics based on the price of the products.

Another focus of oral care and hygiene that has not been addressed by current technology available to humans are the levels of salivary secretory Immunoglobulin A (SIgA). SIgA is the dominant immunoglobulin produced by secretions originating from the epithelial lining that bathe mucosal surfaces (e.g., oral, respiratory, intestinal, and reproductive). SIgA plays a critical role guarding against microbial invasion by inhibiting the attachment of pathogenic microbes to mucosal surfaces. SIgA levels are generally undetectable at birth, elevate rapidly during the first months of life, and continue to increase until stabilizing during childhood (e.g., ages 5-7). SIgA levels may decrease for a variety of reasons including but not limited to aging (e.g., later in adulthood), the presence of stress related conditions, and nutritional deficiencies. Decreases in SIgA poses significant risks considering its critical importance in mucosal resistance to infection.

Conventional treatments for increasing low SIgA levels include nutritional adjustments and lifestyle adjustments for a reduction in stress levels. For example, probiotics, beta glucans and digestive enzymes may be incorporated into the diet to increase the production of SIgA. Additionally, stress relieving techniques such as meditation, yoga and/or other exercise may be incorporated into the daily routine in order to improve SIgA levels.

One challenge associated with conventional nutritional and lifestyle based treatments includes the lengthy amount of time before results appear. For example, it may take on the order of months to years to see an increase in SIgA depending on the starting level of the SIgA. Additionally, conventional nutritional treatments such as probiotics, beta glucans and digestive enzymes may be expensive and thereby have limited accessibility in low resource environments.

In light of the forgoing, it may be desirable to develop alternative options for inhibiting and treating enamel demineralization and increasing SIgA levels alone or concomitantly.

SUMMARY

A first aspect of the disclosure includes a composition for the inhibition and treatment of enamel demineralization, the composition including: a first solution comprising at least 0.01% by weight lithothamnium calcareum (LC), and a second solution comprising an amount of hydrochloric acid (HCL) sufficient to adjust the pH of the composition to a pH within the range of about pH 6.0 to 7.2.

A second aspect of the disclosure is directed to a method of inhibiting or treating enamel demineralization, the method including: exposing a tooth to a first lithothamnium calcareum (LC) containing composition.

A third aspect of the disclosure is related to a method of increasing salivary secretory Immunoglobulin A (SIgA) in a mammal including: topically exposing an oral cavity to a first lithothamnium calcareum (LC) containing composition.

The foregoing and other features of the disclosure will be apparent from the following more particular description of embodiments of the disclosure.

BRIEF DESCRIPTION OF THE DRAWINGS

The embodiments of this disclosure will be described in detail, with reference to the following figures, wherein.

DETAILED DESCRIPTION

In the following description, reference is made to the accompanying figures that form a part thereof, and in which is shown by way of illustration specific embodiments in which the present teachings may be practiced. These embodiments are described in sufficient detail to enable those skilled in the art to practice the present teachings and it is to be understood that other embodiments may be used and that changes may be made without departing from the scope of the present teachings. The following description is, therefore, merely illustrative.

Provided herewith are compositions and methods for the inhibition and treatment of enamel demineralization and the effects of enamel demineralization (e.g., erosion and carious lesions). Also provided herewith are compositions and methods for increasing salivary secretory immunoglobulin (SIgA) levels in the oral cavity of a mammal.

Turning first to the compositions, an embodiment of the present invention provides a composition containing a calcareous marine macroalgae extract. For example, the composition may contain a first solution of lithothamnium calcareum (LC, also known as phymatolithon calcareum) and a second solution of hydrochloric acid (HCL).

Figure 1:
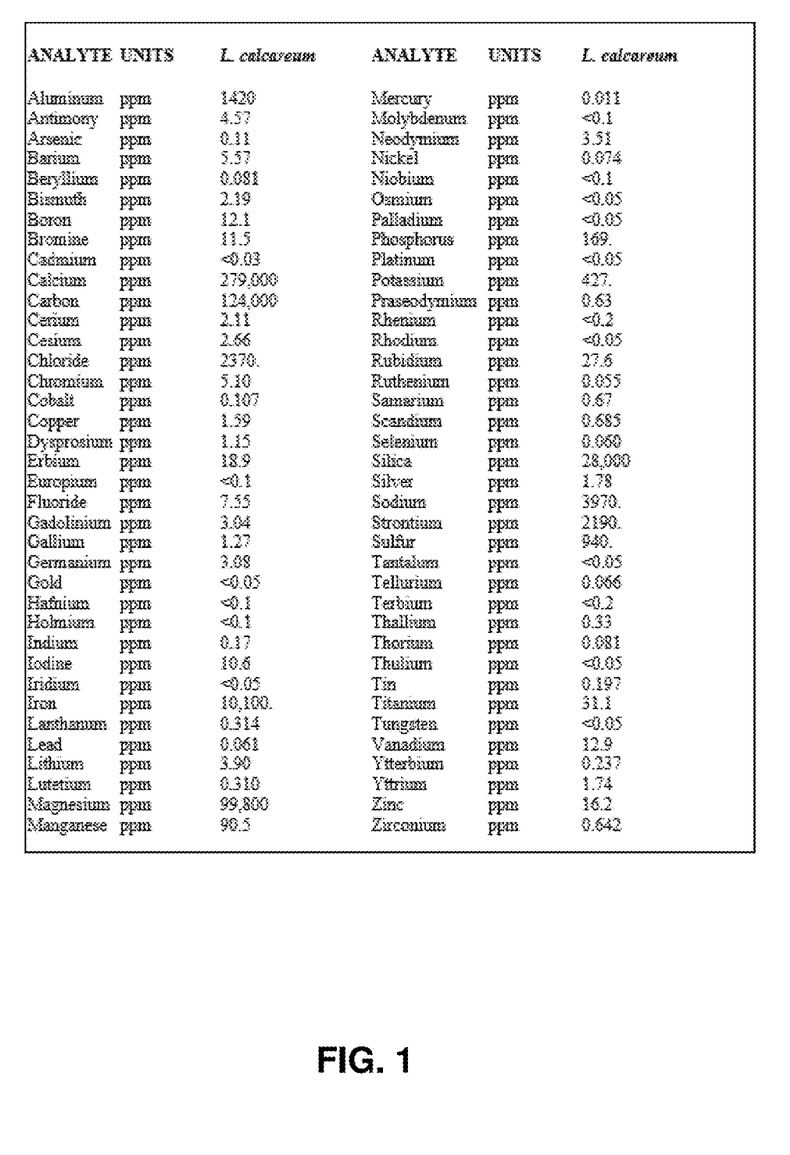
FIG. 1 shows composition analysis results for a lithothamnium calcareum (LC) sample, according to embodiments of the disclosure.

LC is a mineral extract produced through biomineralization by a calcareous macroalgae. Biomineralization is the biological formation of minerals by living organisms. Biogenic minerals are produced by bacteria, fungi, mollusks, sponges, corals, deep-sea benthic species, algae, and other organisms who maintain minerals deposited within themselves and/or in their immediate surroundings as a result of their metabolism. LC is a calcium and phosphate rich natural extract specifically derived from the skeletal remains of the red algae lithothamnium calcareum. FIG. 1 provides a table of the trace elements found in LC extract and their respective amounts in parts per million (ppm). As shown in the table of FIG. 1, the major components of LC extract are calcium and magnesium (i.e. more than 20% and 4% by weight, respectively). As also shown in the table of FIG. 1, LC extract may contain measurable levels of 74 other trace elements, such as phosphorus.

The composition provided herewith may include a first solution having at least 0.01% by weight LC extract, and a second solution having an amount of an acid to adjust the pH of the composition to a pH within the physiological range of pH 6.0 to 7.2. For example, the second solution may contain hydrochloric acid (HCL), sulfuric acid, nitric acid, phosphoric acid, carbon dioxide and/or any other desirable acid for adjusting the pH of the first solution to a physiological value.

For example, the first solution of the composition may include about 0.02 to about 0.03% by weight LC extract, and more specifically at least 0.03% by weight LC extract. The second solution may include, for example, an amount of about 0.1 normal (N) to about 1.0 N HCL to adjust the pH of the composition to about pH 6.0 to 7.2, for example, pH 6.9. As used herein, the term "normal (N)" includes an equivalent concentration of a solution or the molar concentration divided by an equivalence factor. For example, "normal (N)" used as a unit may denote equivalent per liter (eq/L). As discussed above, the second solution may include any concentration of any desirable acid for adjusting the pH of the first solution.

In a first non-limiting example, an LC containing composition according to embodiments of the disclosure may include a first solution containing 0.01% LC extract by weight, and a second solution containing 15 μL of 1 N HCL for every 1 mL of the 0.01% LC containing first solution. This first example of an LC containing composition may be referred to hereinafter as the 0.01% LC composition.

In a second non-limiting example, an LC containing composition according to embodiments of the disclosure may include a first solution containing 0.01% LC extract by weight, and a second solution containing 34 μL of 1 N HCL for every 1 mL of the 0.03% LC containing first solution. This second example of an LC containing composition may be referred to hereinafter as the 0.03% LC composition.

Although two examples of the LC containing composition are given, it is understood that the LC containing composition of the present invention may include a first solution having any amount of LC, and a second solution having any amount of HCL for adjusting the pH of the composition within the physiological range of pH.

Figure 2:
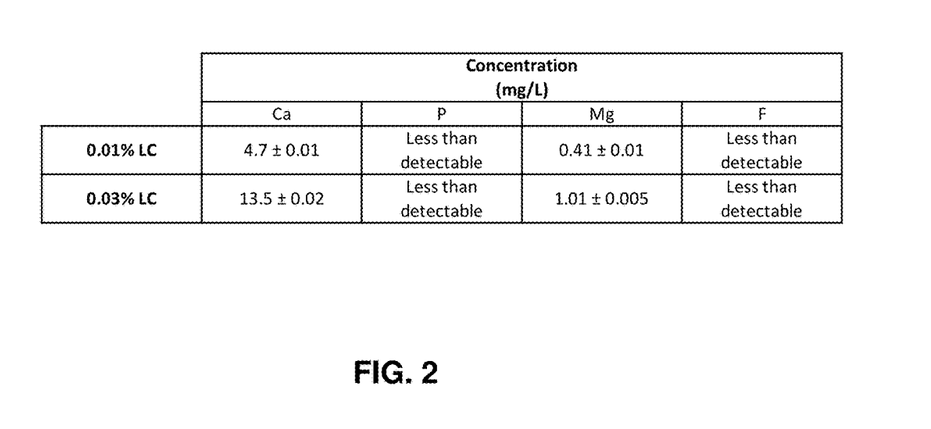
FIG. 2 shows the concentration of particular elements in an LC containing composition, according to embodiments of the disclosure.

Depending on the amount of LC in the first solution, the final composition may contain varying concentrations of Calcium (Ca) and Magnesium (Mg). For example, as shown in the table of FIG. 2, a composition containing a first solution having about 0.01% by weight LC extract may have a concentration of about 4.7 milligrams per liter (mg/L) Ca and about 0.41 mg/L Mg. In contrast, a composition containing a first solution having about 0.03% by weight LC extract may have a concentration of about 13.5 mg/L Ca and about 1.01 mg/L Mg. As shown by the table of FIG. 2, the greater the amount of LC extract in the first solution of the composition, the greater the concentration of the Ca and Mg. For example, the amount of LC extract in the first solution of the composition may be selected based on the desired amount of Mg or Ca in the final composition. As also shown in the table of FIG. 2, the compositions may also contain a less than detectable concentration of phosphorous (P), and fluoride (F) based on their presence in the LC extract.

The composition disclosed herein may optionally include an amount of flavoring and/or sweetening agent. For example, a flavoring such as mint, strawberry, etc., may be optionally incorporated into the composition. A sweetener such as trichloroglactosucrose, xylitol and others may also be optionally added to the composition. The flavoring and/or sweetener may, for example, make the composition more desirable and easier to use in oral exposure treatments. In another non-limiting example, the flavoring and/or sweetener may be natural and/or organic, such as, for example, xylitol, sorbitol, sucralase, stevioside, etc.

The LC containing compositions disclosed herein may improve oral health and general systemic health, for example, by inhibiting enamel demineralization, promoting enamel remineralization, and increasing SIgA levels. For example, the LC containing compositions may increase enamel surface hardness and increase salivary SIgA. The LC containing compositions may therefore also inhibit and/or treat the effects of enamel demineralization, e.g., erosion and/or carious lesions, in the enamel, and guard against infection.

LC extract may provide a safer and healthier alternative to conventional oral care products used to inhibit demineralization, promote remineralization and/or increase SIgA levels. The LC containing compositions provided herein may be free from fluoride and therefore reduce the risk of dental fluorosis. For example, using an LC containing composition may allow for fewer side effects. Additionally, LC extract may be more readily accessible and less expensive to obtain than conventional treatments, allowing for a less expensive alternative that is readily accessible to low resource demographics.

A method for forming the LC containing compositions is also provided herewith. The method may first include solubilizing at least 0.01 grams (g) of LC sieve powder in 100 mL of a diluent. The diluents may include phosphate buffered saline (PBS), distilled water, dimethyl sulfoxide (DMSO), ethanol, and/or any other desirable diluent for solubilizing the selected amount of LC sieved powder. The LC sieved powder may be solubilized in the diluent, for example, at approximately 25 degrees Celsius (i.e., room temperature) by stirring for approximately 30 seconds. Once the solution containing at least 0.01% by weight LC sieved powder is formed, the method may also include titrating the first LC solution to a physiological pH of about pH 6.0 to about 7.9. The solution may be titrated with a prepared hydrochloric acid (HCL) solution and/or any other desirable solution for adjusting the pH to a physiological level. The HCL solution may be prepared by conventional techniques and may include any desirable molarity and volume. In non-limiting examples, the solution may alternatively be titrated using acids such as sulfuric acid, nitric acid, phosphoric acid, and carbon dioxide solutions.

In a first non-limiting example, a method for forming the 0.01% LC composition discussed above is described. First, about 0.01 grams of LC sieved powder and 100 mL of distilled water may be combined. The combination may be mixed, for example, at approximately 25 degrees Celsius (i.e., room temperature) by stirring for approximately 30 seconds to form the first solution of the composition. Next, a second solution containing HCL may be formed or provided. For example, approximately 123 µL of 1N HCL may be provided. In another non-limiting example, approximately 739 µL of 0.1 N HCL may alternatively be provided. Next, the first solution containing 0.01% LC may be titrated with the second HCL solution to reach a pH of 6.9 and form the 0.01% LC composition.

In a second non-limiting example, a method for forming the 0.03% LC composition discussed above is described. First, about 0.03 grams of LC sieved powder and 100 mL of distilled water may be combined. The combination may be mixed, for example, at approximately 25 degrees Celsius (i.e., room temperature) by stirring for approximately 30 seconds to form the first solution of the composition. Second, a second solution containing HCL may be formed or provided. For example, approximately 173 µL of 1N HCL may be provided. In another non-limiting example, approximately 822 µL of 0.1N HCL may alternatively be provided. Next, the first solution containing 0.03% LC may be titrated with the second HCL solution to reach a pH of 6.9 and form the 0.03% LC composition.

Although two methods are described herein, similar steps with different amounts and volumes of solvents and diluents may be performed without departing from the scope of the invention encompassed by the appended claims.

Methods for inhibiting and treating enamel demineralization are also provided herewith. Methods for increasing salivary secretory concentrations of secretory Immunoglobulin A (SIgA) are also provided herewith. The methods may include a topical and/or systemic application of an LC containing composition to a tooth. As used herein, the term "topical" may include local or surface exposure of a tooth to a substance. For example, "topical" may include rinsing, soaking, coating, etc. the surface of the tooth with an LC containing composition. As used herein, the term "systemic application" or "systemic exposure" may include exposing a tooth to a substance through delivery by way of the circulatory system of the mammal containing the tooth. For example, "systemic exposure" may include exposing a patient's tooth to a LC containing composition by oral consumption, injection, transdermal application, etc., of the LC containing composition to the patient and delivery of a portion of the LC containing composition to the tooth through the patient's circulatory system. Although the methods described herein are explained with reference to studies using LC containing compositions having a particular % by weight of LC and a particular pH, it should by understood by those skilled in the art that various changes in form and details of the composition may be made herein without departing from the scope of the invention encompassed by the appended claims. Additionally, although the methods described herein include topical exposure by rinsing and soaking, and systemic exposure by oral ingestion, it is understood by those skilled in the art that the type of topical and/or systemic exposure may be varied (e.g., the tooth may be soaked instead of coated, or the LC containing composition may be intravenously injected instead of orally consumed) without departing from the scope of the invention encompassed by the appended claims.

The following are examples of methods for inhibiting demineralization, promoting remineralization and/or increasing SIgA levels. Specifically, the following examples include applying the LC containing composition discussed above to tooth specimens and/or oral cavities, according to embodiments of the disclosure. Example 1 relates to the inhibition and treatment of enamel demineralization by coating of an intact tooth and a caries affected tooth in an LC containing composition, as tested in vitro. Example 2 relates to the inhibition and treatment of enamel demineralization by repeated rinsing of a caries affected tooth in an LC containing composition, as tested in vivo. Example 3 relates to the inhibition and treatment of enamel demineralization by repeating rinsing of a caries affected tooth and optional ingestion of LC containing compositions, as tested in vivo. Example 4 relates to increasing SIgA by repeated rinsing of an oral cavity and optional ingestion of LC containing compositions, as tested in vivo. Other non-limiting examples of methods may include, for example, application of the LC containing composition to a tooth and/or oral cavity by inclusion of the composition in toothpaste, slow release devices, nanoparticles, bone grafts, intracanal (endodontic cements), dental cements, chewing gum, candy, beverages, milk, food preparations, etc.

EXAMPLE 1

A first method of inhibiting and treating enamel demineralization may include coating a tooth in a LC containing composition for at least 30 seconds at least once a day for at least one day. In a non-limiting example, the tooth may be coated in a 0.01% LC composition for at least five minutes twice a day for six days. In another non-limiting example, the tooth may be coated in a 0.03% LC composition for at least five minutes twice a day for six days.

The coating may be applied by syringe, brush, or any other common application tools. The method may optionally include drying the tooth at the end of each coating treatment. Additionally, the tooth may also optionally be subjected to mechanical treatment to further aid in inhibiting and treating enamel demineralization. Mechanical treatment may include scraping, rubbing, brushing, flossing or combinations thereof. The mechanical treatment may be performed before or after the coating and/or optional drying of the tooth. In a non-limiting example, the coating treatment may be accompanied by brushing the tooth for at least 30 seconds after drying the tooth.

The above method was tested by an in vitro study where a tooth was coated for approximately five minutes twice a day for six days, and dried at the end of each coating treatment. Two preparations of LC containing compositions were formed according to the methods of the disclosure described above. Specifically, the 0.01% LC and the 0.03% LC compositions were formed. A positive control solution of 0.05% by weight sodium fluoride (NaF) and a negative control solution of distilled water were also prepared, by conventional techniques.

Two hundred teeth in the form of bovine incisors with complete root formation were obtained and stored in 0.9% sodium chloride (NaCl) solution for a week. The teeth were then washed in water and the crowns separated therefrom. Similarly sized fragments from each crown were prepared (e.g., 4 millimeters (mm) by 4 mm by 2.5 mm). The enamel surface of the fragments was ground flat with silicon carbide paper and then polished with wet felt paper using diamond spray. The surface hardness of each specimen was measured before any further processing. For example, the surface hardness was measured using a hardness indenter with a sample size of five indentations per specimen. The indentations were performed approximately 100 micrometers apart from one another.

Approximately half of the specimens were randomly selected for a group of intact enamel specimens, and the remaining half of the samples were induced with artificial caries lesions for a group of caries induced specimens. The caries lesions were induced by known protocols for the development of artificial lesions. The surface hardness of the caries induced specimens was again measured following caries lesion induction. For example, another five indentations were performed.

The intact specimens and caries induced specimens were randomly assigned to four groups for treatment with the different preparations discussed above. For example, group one was treated with the 0.01% LC composition, group two was treated with the 0.03% LC composition, group three was treated with the positive control (0.05% by weight NaF), and group four was treated with the negative control (distilled water). A substantial portion of the specimen surfaces of each group were coated with the respective treatment preparation and kept undisturbed twice a day for approximately five minutes at a time. Between coating treatments, the teeth were immersed in a demineralizing solution for approximately 6 hours. During a remainder of each 24 hour period, i.e. approximately 18 hours, the teeth were immersed in a remineralizing solution. The rotating immersion in demineralizing solution and remineralizing solution allowed for an in vivo environment to be mimicked.

Following the completion of the six cycles, the surface hardness and cross-sectional hardness of each specimen, both intact and caries induced, was measured. The surface hardness was measured by the same method of five indentations as previously discussed. The cross-sectional hardness of each specimen was measured by longitudinal sectioning and indenting with a sample size of three rows of eight indentations per sample.

Figure 3:
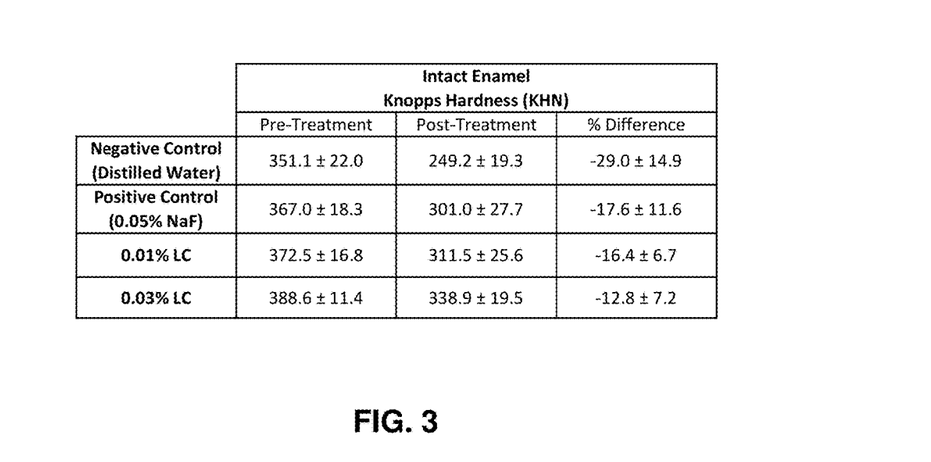
FIG. 3 shows surface hardness results for intact enamel treated with various compositions, according to embodiments of the disclosure.

Referring to the table of FIG. 3, a summary of the surface hardness measurements for the intact specimens is shown. Specifically, the table shows the average Knoop hardness value (KHN) for pre-treatment, post-treatment, and the change there between for the specimens in each group. As shown in the table of FIG. 3, treatment of the intact tooth samples with the LC containing compositions reduced the amount of surface hardness lost and thus inhibited enamel demineralization by a greater amount than treatment with the negative control, i.e. distilled water. Additionally, treatment with the higher concentration (0.03% LC) composition showed a higher tendency for inhibiting at least partial reduction in surface hardness as compared to the 0.01% LC composition and the positive control, 0.05% NaF. Although to a lesser extent as compared to the 0.03% LC composition, the 0.01% LC composition also shows a higher tendency for inhibiting at least partial surface hardness reduction compared to the positive control, 0.05% NaF. These results confirm that treatment of an intact tooth by coating with an LC containing composition inhibits surface hardness reduction in enamel and inhibits enamel demineralization. Specifically, application of an LC containing composition by coating inhibits excessive loss of minerals by tooth enamel. Additionally, these results confirm that the higher the concentration of the LC extract in the composition, the greater the inhibition of demineralization.

Figure 4:
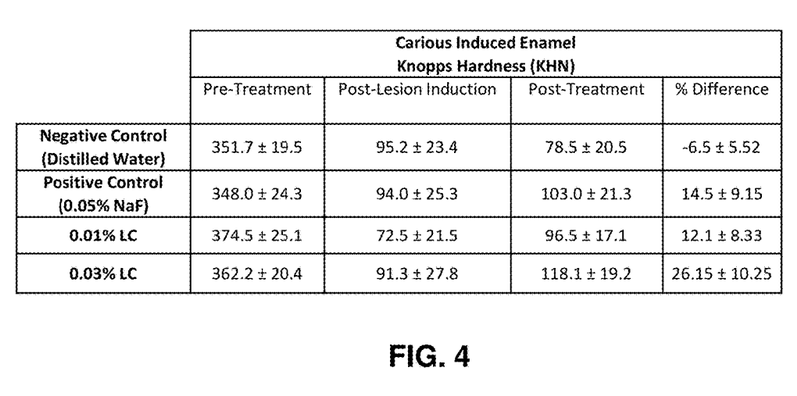
FIG. 4 shows surface hardness results for carious induced enamel treated with various compositions, according to embodiments of the disclosure.

Referring next to the table of FIG. 4, a summary of the surface hardness analysis for the caries induced specimens is shown. Specifically, the table shows the average Knoop hardness value (KHN) pre-treatment (and pre-lesion induction), post-lesion induction, post-treatment, and the change between the post-lesion induction values and post-treatment values for the specimens in each group. As shown in the table of FIG. 4, treatment of the caries affected specimens with the LC containing compositions increased enamel surface hardness and promoted enamel remineralization as compared to tooth samples treated with the negative control, i.e. distilled water. Additionally, treatment with the higher concentration 0.03% LC composition showed a greater increase in enamel surface hardness and remineralization as compared to the 0.01% LC composition and the positive control, 0.05% NaF. These results confirm that treatment of a caries affected tooth by coating in an LC containing composition increases enamel surface hardness and promotes enamel remineralization. For example, the concentration of calcium in the LC of the LC containing composition may replenish the physiological concentration of calcium in the oral or biofilm fluids, and promote enamel remineralization. Additionally, the concentration of magnesium (Mg) in the LC of the LC containing composition may assist in regulating the development and mineralization of tooth enamel. These results also confirm that the higher the concentration of the LC extract in the composition, the greater the promotion of remineralization.

Figure 5:
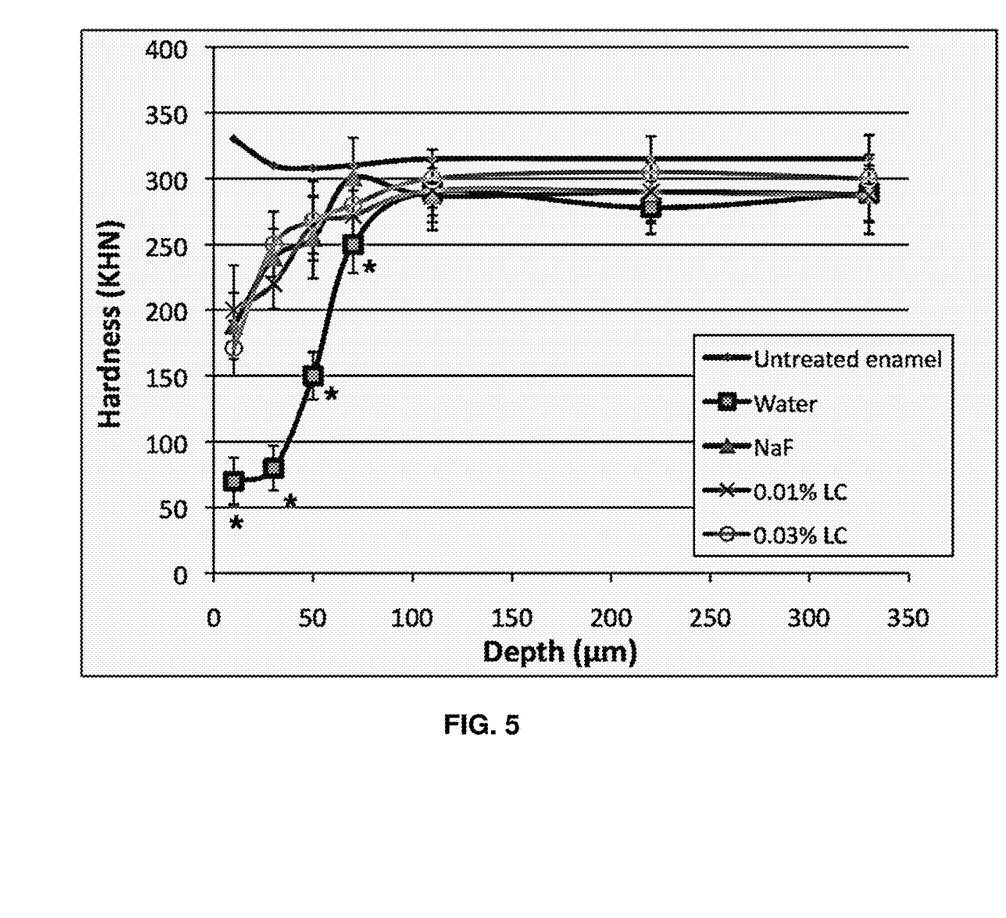
FIG. 5 shows cross-sectional surface hardness results for intact enamel treated with various compositions, according to embodiments of the disclosure.

Referring to the graph of FIG. 5, a summary of the cross-sectional hardness measurements for the intact specimens is shown. Specifically, the graph of FIG. 5 shows the Knoop hardness values across the cross-section of the intact tooth samples after treatment with 0.01% LC, 0.03% LC, the negative control (distilled water), and the positive control (0.05% NaF). As evidenced by the results, the LC containing compositions significantly reduced hardness loss and mineral loss of the intact samples up to a 70 micrometer (μm) depth into the enamel as compared to treatment with the negative control, i.e. distilled water. These results confirm that LC containing compositions inhibit hardness loss and demineralization of intact enamel. Additionally, these results further confirm that the higher the concentration of the LC extract in the composition, the greater the inhibition of demineralization.

Figure 6:
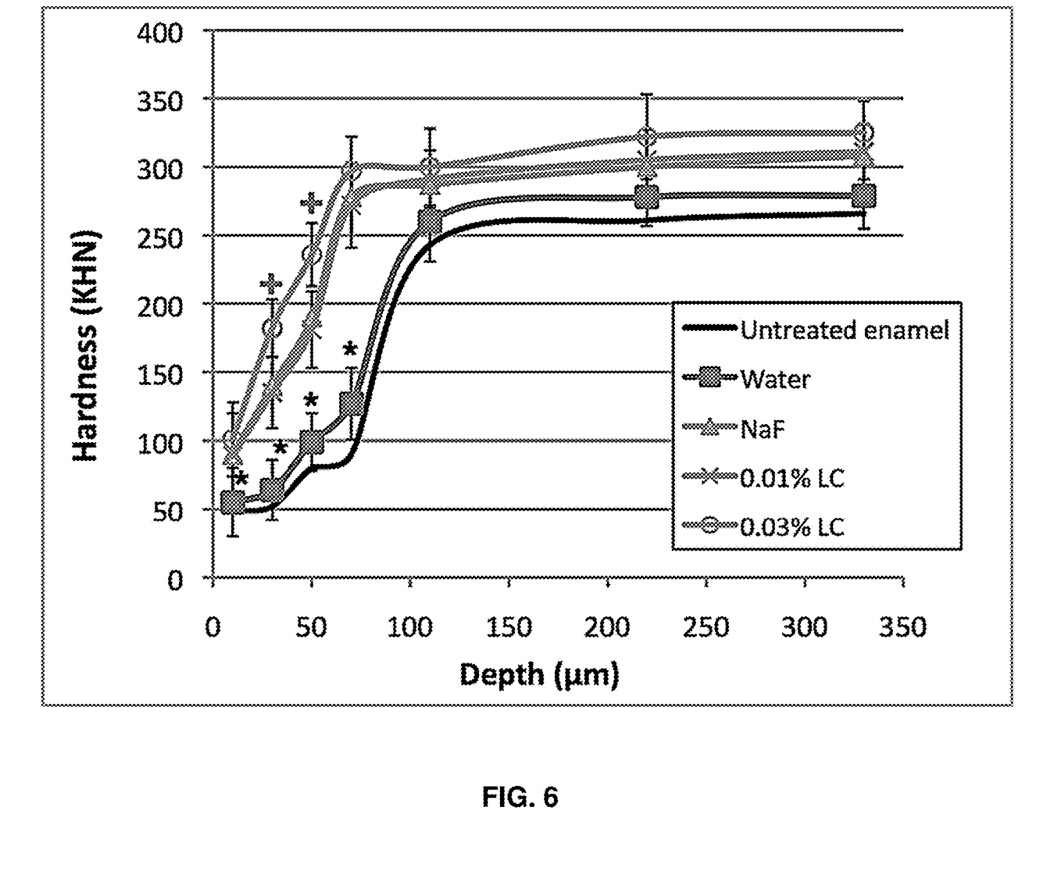
FIG. 6 shows cross-sectional surface hardness results for carious induced enamel treated with various compositions, according to embodiments of the disclosure.

Referring to the graph of FIG. 6, a summary of the cross-sectional hardness measurements for the caries induced specimens is shown. Specifically, the graph of FIG. 6 shows the Knoop hardness values across the cross-section of the caries induced specimens after treatment with 0.01% LC, 0.03% LC, the negative control (distilled water), and the positive control (0.05% NaF). Similarly to the results shown in the graph of FIG. 5 for intact specimens, the cross-sectional hardness measurement results in the caries affected specimens indicate that the LC containing compositions significantly reduced hardness loss of the caries induced tooth samples up to a 70 micrometer (μm) enamel depth as compared to treatment with the negative control, i.e. distilled water. These results again confirm that LC containing compositions inhibit hardness loss and demineralization, and promote remineralization of caries affected enamel. Additionally, the result further confirms that a higher concentration of LC in the composition may increase the amount of demineralization inhibition and remineralization promotion.

EXAMPLE 2

A second method of inhibiting and treating enamel demineralization may include rinsing a tooth in a LC containing composition for at least 30 seconds at least once a day for at least one week. In a non-limiting example, the method may include rinsing a tooth in an LC containing composition for about 45 seconds twice a day for two weeks. The method may optionally include subjecting the tooth to mechanical treatment to further aid in inhibiting and treating enamel demineralization. Mechanical treatment may include scraping, rubbing, brushing, flossing or combinations thereof. The mechanical treatment may be performed before or after the coating and/or optional drying of the tooth. In a non-limiting example, the coating treatment may be accompanied by brushing the tooth for at least 30 seconds.

The second method was tested using the following in vivo study where caries affected tooth samples were rinsed with 0.03% LC, a positive control (0.05% NaF), and a negative control (distilled water) for about 45 seconds twice a day for two weeks. A 0.03% LC composition was prepared according to the methods previously discussed herein for forming a 0.03% LC composition. The same positive control solution (0.05% by weight (NaF)) and a negative control solution (distilled water) as in Example 1 were also prepared.

Samples of bovine incisors were obtained, stored and prepared by the same methods as the study of Example 1. Similarly to Example 1, the surface hardness of each sample was measured by the same indentation protocol prior to any further processing. In contrast to the study of Example 1, all of the specimens were subjected to the caries induction processes of the study of Example 1. The surface hardness of each specimen was re-measured following the induction of caries lesions therein. Additionally, the enamel of each specimen was subjected to a quantitative light-induced fluorescence (QLF) technique to obtain images for assessment of the demineralization status of the enamel. As used herein, a QLF technique may include the collection of images of a sample over time, and the analysis of the differences between pixel values of the enamel to determine the presence and amount of demineralization. For example, the QLF technique variables may include average fluorescence loss, size of the lesion, fluorescence loss with respect to the lesion size, etc.

The caries specimens were next placed in bilateral lodges of acrylic intraoral palatal appliances. Specifically, two specimens were included at random positions on each of two sides of the palatal appliances. The appliances were sterilized and provided to study participants. The study participants who completed the study included 26 pairs of twins and one set of triplets between the ages of 12 and 24 years old. The benefit of using twins in the study includes, in non-limiting examples (1) control of environmental factors (e.g., diet, lifestyle, etc.); (2) reduction of bias often associated with the use of unrelated individuals in case-control studies; (3) control over factors leading to dental caries; and (4) increase in cost efficiency. The study participants kept the intra-oral palatal appliances in place except for during main meals where the appliances were removed from the oral cavity for a maximum duration of one hour per meal.

A first member of each twin pair was assigned to the experimental test group and the second member of each twin pair was assigned to the control group. The twin members in the experimental test group rinsed the oral cavity including the specimens in the appliances with the 0.03% LC composition for approximately 45 seconds twice a day for two weeks. A first portion of the twin members in the control group performed the same rinsing routine except with the positive control, i.e. 0.05% NaF solution, instead of the LC containing composition. A second portion of the twin members in the control group performed the same rinsing routine except with the negative control, i.e. distilled water. The study participants also continued their normal oral hygiene practices throughout the study such as, for example, brushing and/or flossing the teeth of the oral cavity.

Following the completion of the two week rinsing routine, the surface hardness of each specimen was re-measured. Additionally, the enamel of each specimen was again subjected to the QLF technique to obtain a second set of images for assessment of the demineralization status of the enamel.

Figure 7:
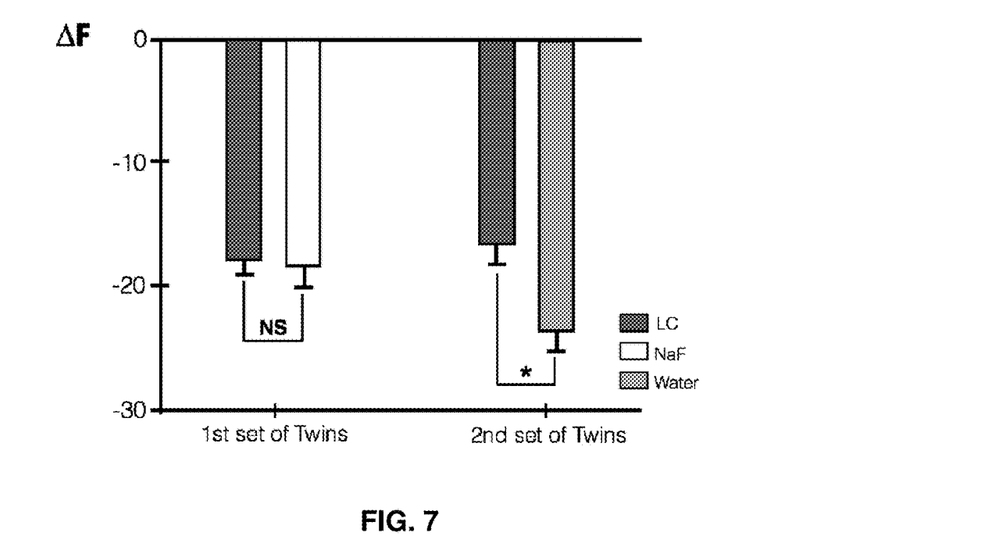
FIGS. 7 and 8 show quantitative light-induced fluorescence QLF results for carious induced enamel treated with various compositions, according to embodiments of the disclosure.
Figure 8:
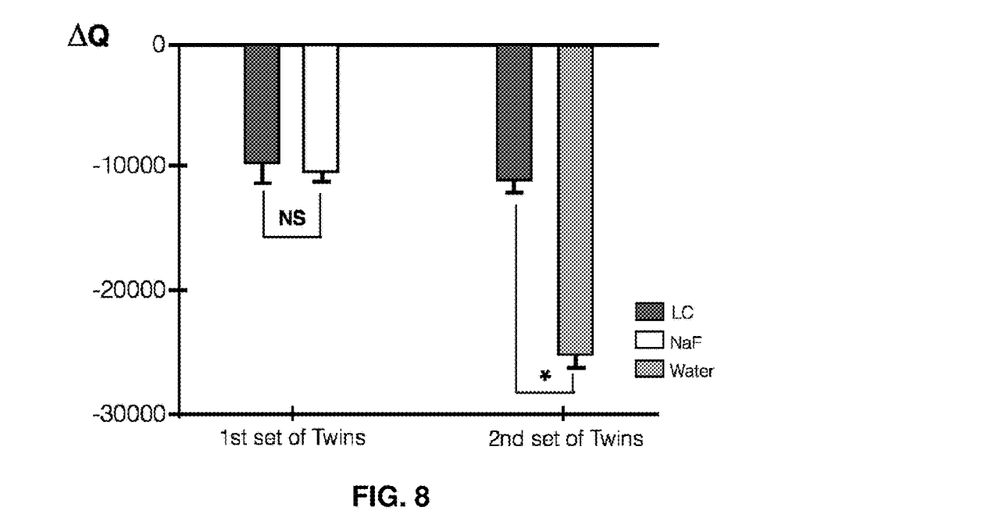

Referring next to the graphs of FIGS. 7 and 8, a summary of the QLF analysis for the specimens is shown. Specifically, the graph of FIG. 7 shows the amount of fluorescence signal (pixel difference, $\Delta F$) which allows for quantitation of enamel mineral loss for both the experimental test group specimens and the control group specimens. The graph of FIG. 8 shows $\Delta Q$ (i.e. the product of $\Delta F$ with the lesion area) for both the experimental test group specimens and the control group specimens. Compared to both the positive control (0.05% NaF) and the negative control (distilled water), treatment with the LC containing composition improved both the $\Delta F$ and $\Delta Q$ values indicating the tendency of the LC containing composition to inhibit mineral loss (demineralization) and promote enamel remineralization in caries affected teeth. The improvement in $\Delta F$ and $\Delta Q$ was most prominent as compared between treatment with the LC containing composition and the negative control (distilled water) treatments. The results confirm that treatment of a caries affected tooth by rinsing with the LC containing composition inhibits demineralization and promotes remineralization.

Figure 9:
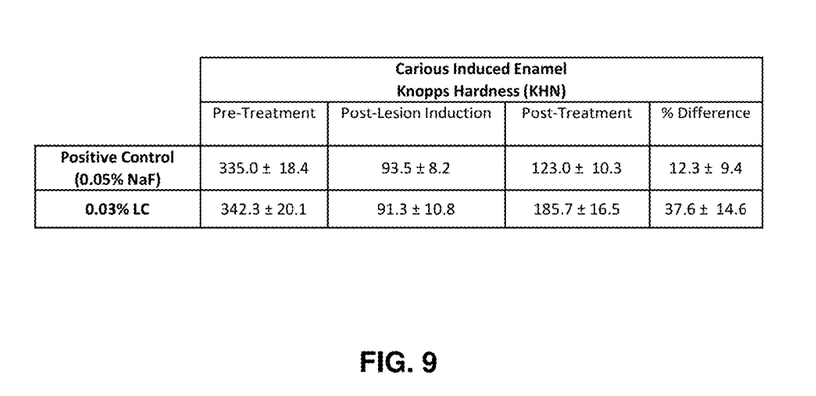
FIG. 9 shows surface hardness results for carious induced enamel treated with LC compositions, according to embodiments of the disclosure.

Referring to the table of FIG. 9, a summary of the surface hardness measurements for the specimens of the group of twins treated with the 0.03% LC composition and positive control (0.05% NaF) is shown. Specifically, the table shows Knoop hardness values of the caries affected specimens pre-lesion induction, post-lesion induction, post-treatment and the difference in enamel surface hardness between post-lesion induction and post-treatment for both sets of specimens. As evidenced by the results, treatment with the LC containing composition improved surface hardness by a greater amount than treatment with the 0.05% NaF solution. The results further confirmed that rinsing of a caries affected tooth with an LC containing composition promotes remineralization.

Figure 10:
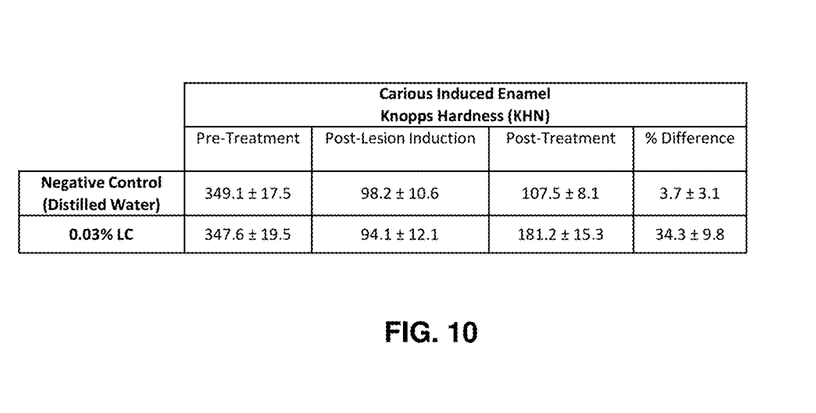
FIG. 10 shows surface hardness results for carious induced enamel treated with LC compositions, according to embodiments of the disclosure.

Referring to the table of FIG. 10, a summary of the surface hardness measurements for the specimens of the group of twins treated with the 0.03% LC composition and the negative control (distilled water) is shown. Specifically, the table shows Knoop hardness values of the caries affected specimens pre-lesion induction, post-lesion induction, post-treatment and the difference in enamel surface hardness between post-lesion induction and post-treatment for both sets of specimens. As evidenced by the results, treatment with the LC containing composition improved surface hardness by a significantly greater amount than treatment with the negative control (distilled water). The results further confirm that rinsing of a caries affected tooth with an LC containing composition promotes remineralization.

EXAMPLE 3

A third method of inhibiting and treating enamel demineralization may include rinsing a tooth in a LC containing composition for at least 30 seconds at least once a day for at least a week, and systemically exposing the tooth to a LC containing composition at least once a day for the same week. For example, a mammal may orally ingest, inject, or dermally apply an LC containing composition once a day while also rinsing the tooth in an LC containing composition. In a non-limiting example, the method may include rinsing a tooth in a 0.03% LC for about 45 seconds twice a day for 8 weeks, and orally ingesting a 500 mg LC capsule twice a day for the 8 weeks. The method may optionally include subjecting the tooth to mechanical treatment to further aid in inhibiting and treating enamel demineralization. Mechanical treatment may include scraping, rubbing, brushing, flossing or combinations thereof. The mechanical treatment may be performed before or after the coating and/or optional drying of the tooth. In a non-limiting example, the coating treatment may be accompanied by brushing the tooth for at least 30 seconds. Applying mechanical treatment may, for example, remove cariogenic microbiome and partly dissolved portions of the enamel surface to further promote enamel remineralization.

The third method was tested using the following in vivo study where a tooth was rinsed with 0.03% LC for approximately 45 seconds twice a day for 8 weeks, and some of the participants also orally ingested a 500 mg LC capsule twice a day for the 8 weeks.

The same 0.03% LC composition as the studies in Examples 1 and 2 was prepared. A capsule containing 500 milligrams (mg) of LC sieved powder was also obtained. The participants to the study included an initial group of 200 children and a final group of 174 of the initial 200 children aged 7-12. The teeth of the participants were examined by trained personnel for the presence of white spot lesions prior to beginning the study treatment.

Participants of the study were randomly assigned to an experimental group and a positive control group. The participants in the experimental group rinsed their oral cavities with the 0.03% LC composition for about 45 seconds twice a day for eight weeks. The participants in the experimental group also orally ingested the 500 mg LC capsule twice a day for the same eight weeks. The participants in the positive control group performed the same 0.03% LC rinsing regimen as the participants in the experimental group. The positive control group participants were not systemically exposed to an LC containing composition, i.e. the participants of the positive control group did not ingest the 500 mg LC capsule. Both groups of participants also brushed their teeth twice a day with a non-fluoridated toothpaste for the same eight weeks. Both groups of participants maintained the remainder of their normal oral hygiene routine. The participants' teeth were again examined for the presence of white spot lesions following the eight weeks of treatment under the study.

Figure 11:
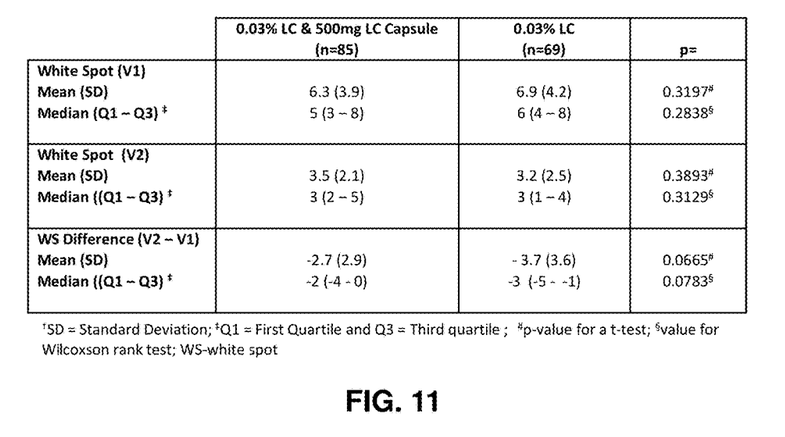
FIG. 11 shows white spot analysis results for carious induced enamel treated with LC compositions, according to embodiments of the disclosure.

Referring to the table of FIG. 11, a summary of the white spot lesion analysis for all participants is shown. The table shows the median and mean values for the difference in the number of demineralized (white spot) lesions from before treatment to after treatment. Specifically, the values are listed for treatment with either the 0.03% LC and 500 mg oral LC capsule, or the 0.03% LC alone. The results revealed that both sets of participants exhibited an overall mean and median decrease in the number of demineralized lesions following treatment. The results again confirm that topically exposing a caries affected tooth with a LC containing composition, such as by rinsing, promotes enamel remineralization of the caries lesions therein. For example, the concentration of calcium and/or magnesium in the LC containing composition may increase their respective concentrations in the oral fluid and dental plaque contacting the caries tooth, which may re-precipitate mineral ions on the enamel surface to allow enamel nanocrystallites to incorporate larger amounts of carbonate ions and trace amounts of the elemental components of the LC containing composition. Rinsing with the LC containing composition may aid in hardening the enamel surface and inhibiting dental caries formation in teeth of mammals.

The results also revealed that the participants who rinsed with the LC containing composition and orally ingested the 500 mg oral LC capsule exhibited a lower mean/median difference in the number of demineralized lesions from before treatment to after treatment as compared to participants that only rinsed with the 0.03% LC composition. Specifically, participants who rinsed with the LC containing composition and orally ingested the 500 mg oral LC capsule had an increased average number of lesions that remineralized than those who only rinsed with the 0.03% LC composition. Exposing a caries affected tooth topically to an LC containing composition, in addition to systemic exposure may therefore even further promote enamel remineralization of caries lesions as compared to topical exposure alone. Specifically, rinsing with and orally ingesting an LC containing composition may increasingly promote enamel remineralization as compared to ingesting the LC containing composition alone. For example, both LC containing compositions may cause an increase in SIgA which may decrease levels of acid-producing bacteria and further enable enamel remineralization.

Similarly to the study in Example 2, the participants of the study of Example 3 continued to perform their usual oral hygiene routines including, for example, brushing their teeth for at least 60 seconds twice a day. Mechanical treatment of caries affected teeth, in addition to rinsing with an LC containing composition, may further inhibit enamel demineralization and promote enamel remineralization.

EXAMPLE 4

A method of increasing SIgA concentrations in a mammal may include rinsing an oral cavity with a LC containing composition for at least 30 seconds at least once a day for at least one week. In a non-limiting example, the method may include rinsing the oral cavity in a 0.03% LC composition for about 45 seconds twice a day for 8 weeks. Another method of increasing SIgA concentrations according to embodiments of the disclosure may include, rinsing an oral cavity with a LC containing composition for at least 30 seconds at least once a day for at least one week and also systemically exposing the cavity to a LC containing composition at least once a day for at least a week. For example, a mammal may orally ingest, inject, or dermally apply an LC containing composition once a day while also rinsing the oral cavity with an LC containing composition. In another non-limiting example, the method may include rinsing an oral cavity with a 0.03% LC composition for about 45 seconds twice a day for eight weeks, and orally ingesting a 500 mg LC capsule twice a day for the same eight weeks.

The above methods were tested using the following in vivo study where an oral cavity with rinsed with 0.03% LC for about 45 seconds twice a day for eight weeks, and some participants also orally ingested a 500 mg LC capsule.

The same 0.03% LC composition as the studies of Examples 1-3 was prepared. A capsule containing 500 milligrams (mg) of LC sieved powder was also obtained, similarly to the study of Example 3. The participants of the study included a group of 48 children aged 7-12. The concentration of SIgA in the participant's saliva was measured prior to beginning the study treatment. Specifically, salivary flow rates were determined and salivary samples were collected while the participants were seated with head tilted and salivary samples dripped off the lower lip into a pre-weighed container. The participants did not eat for at least an hour before the collection and were asked not to swallow or move the tongue or lips during the collection period. The collection period took approximately three minutes. The volume of the sample was measured gravimetrically, and the flow rate determined. SIgA levels were measured by particle enhanced nephelometric immunoassay (PENIA) on a nephelometer, taking the salivary flow rate into account. Specifically, the concentration of SIgA was multiplied by the salivary flow rate for a measure per unit time.

Participants of the study were randomly assigned to an experimental group and a positive control group. The participants of each group were subjected to the same treatment conditions as described above with respect to Example 3. Both groups of participants maintained their normal oral hygiene routine. Salivary samples and salivary flow rate were again collected after treatment by the same techniques as described above for the first set of samples. Referring to the table of FIG. 12, a summary of the SIgA level results for all participants is shown. Specifically, the table shows the median SIgA levels (µg/min) before treatment and after treatment with either the 0.03% LC and 500 mg oral LC capsule, or the 0.03% LC alone. The results take into account age differences of the specimens and the associated natural differences in SIgA. The table also shows the median SIgA levels six months after the end of treatment for both the 0.03% LC and 500 mg oral LC capsule, and the 0.03% LC only treatments.

Figure 12:
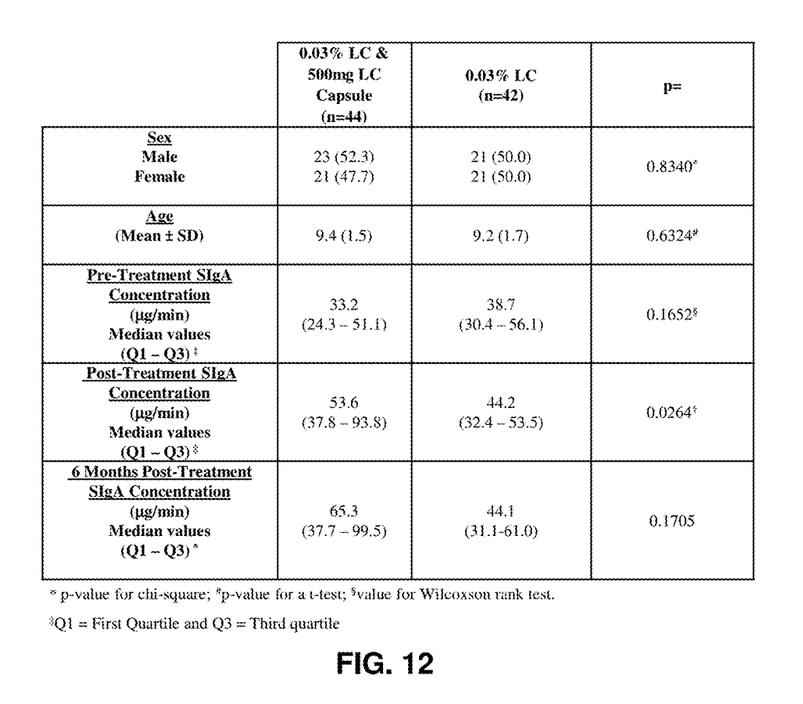
FIGS. 12 and 13 show salivary secretory immunoglobulin A (SIgA) level results for oral cavities treated with LC containing compositions, according to embodiments of the disclosure.

The results revealed that the participants that underwent either or both topical and/or system exposure to an LC containing composition (e.g., rinsing with and/or orally ingesting the LC containing composition) exhibited higher median SIgA levels following treatment. These results confirm that exposing an oral cavity topically (e.g., by rinsing) to an LC containing composition promotes an increase in SIgA levels. For example, topically exposing an oral cavity to an LC containing composition, e.g., by rinsing, may improve synthesis of SIgA by plasma cells within salivary glands. Topical exposure of the oral cavity to an LC containing composition may therefore enhance the mucosal immune system. Additionally the results confirmed that rinsing and/or orally ingesting a LC containing composition may result in an increase in SIgA in as few as 8 weeks following the start of treatment.

The results also revealed that the participants who rinsed with the LC containing composition and orally ingested the 500 mg oral LC capsule exhibited a greater median value of SIgA levels as compared to participants that only rinsed with the 0.03% LC composition. As confirmed by these results, exposing an oral cavity both topically (e.g., by rinsing) and systemically (e.g., by oral ingestion) to an LC containing composition may even further promote an increase in SIgA levels. For example, systemically consuming LC containing compositions in combination with topical exposure may synergistically enhance the synthesis of SIgA on the oral mucosal surface.

The results also revealed continuously increasing SIgA levels up to six months after the treatment had ended. These results confirmed that exposing an oral cavity topically and/or systemically to an LC containing composition may allow for residual increases in SIgA up to at least six months following the end of the treatment.

Figure 13:
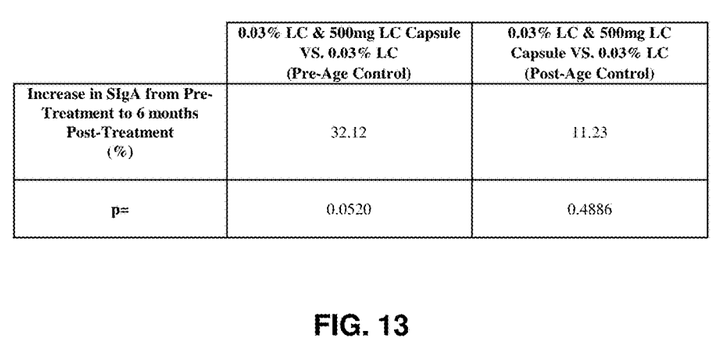

Turning to the table of FIG. 13, a summary of differences in the increased levels of SIgA is presented between the two different treatment regimens from pre-treatment to six months post treatment. Specifically the table shows a percent increase for both topical and systemic treatment as compared to only topical treatment, before and after taking into consideration the natural differences in SIgA based on age. The results revealed that exposure both topically and systemically caused a 32.12% increase in SIgA levels over only topical treatment, before taking into consideration the age differences of the specimens. The results also revealed that exposure both topically and systemically correlated with a 11.23% increase in SIgA levels over only topical treatment, after taking into consideration the age differences. The results confirm that topically and systemically exposing an oral cavity to an LC containing composition may result in a greater increase in overall SIgA levels compared to only systemic treatment, irrespective of the age of the participant. Specifically, rinsing with and orally consuming LC containing compositions may increase overall SIgA to a greater extent than only systemically exposure to an LC containing composition.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s). As used herein, the term "substantially trapezoidal" may refer to a shape having four major sides with two of the major sides being parallel to one another, but with some variation in the shape of the segments and/or the number of minor sides. As used herein, the term "substantially triangular" may refer to a shape having three major sides but with some variation in the shape of the segments and/or the number of minor line segments. As used herein, the term "substantially vertical" may include an angle of 90 degrees+/−10% with respect to the surface of reference. As used herein, the term "substantially slanted" may include an angle greater or less than the 90 degrees+/−10%.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A composition for the inhibition and treatment of enamel demineralization, the composition comprising:
   a first solution comprising at least 0.01% by weight lithothamnium calcareum (LC), and
   a second solution comprising an amount of an acid sufficient to adjust the pH of the composition to a pH within the range of about pH 6.0 to 7.2.

2. The composition of claim 1, wherein the second solution is about 0.01 N to about 1 N hydrochloric acid (HCL).

3. The composition of claim 2, wherein the first solution comprises about 0.01 to about 0.03% by weight LC.

4. The composition of claim 1, wherein:
   the first solution comprises about 0.03% by weight LC,
   the composition comprises about 100 milliliters (mL) of the first solution,
   the second solution is 0.1 N HCL,
   the composition comprises about 739 µL of the second solution, and
   the pH of the composition is about 6.9.

5. The composition of claim 1, wherein the composition is one of a liquid, a paste, or a gel.

6. A method of inhibiting or treating enamel demineralization, the method comprising:
   exposing a tooth to a first lithothamnium calcareum (LC) containing composition.

7. The method of claim 6, wherein the tooth is exposed to the first LC containing composition at least once a day for at least one week.

8. The method of claim 6, wherein the exposing the tooth to the first LC containing composition is by one of rinsing, coating, spraying, or immersing the tooth with the first LC containing composition.

9. The method of claim 6, wherein the tooth is rinsed with the first LC containing composition for at least about 30 seconds at least once a day for at least one week.

10. The method of claim 6, wherein the first LC containing composition comprises a first solution, the first solution comprising at least 0.01% LC by weight.

11. The method of claim 6, wherein the tooth is topically exposed to the first LC containing composition and wherein the tooth is also systemically exposed to a second LC containing composition.

12. The method of claim 11, wherein the tooth is systemically exposed to the second LC containing composition by:
   oral ingestion of the second LC containing composition by a mammal containing the tooth, or
   injection of the second LC containing composition by a mammal containing the tooth.

13. The method of claim 11, wherein:
   the second LC containing composition is a capsule containing about 250 milligrams (mg) to about 1000 mg of LC in the form of a powder; and
   the tooth is systemically exposed to the second LC containing composition by oral ingestion of the second LC containing composition by a mammal containing the tooth, the oral ingestion being at least once a day for at least one week.

14. The method of claim 6, wherein the tooth is substantially coated in the first LC containing composition for at least 60 seconds at least one time per day for at least one week.

15. The method of claim 14, wherein the tooth is substantially coated in the first LC containing composition for at least 5 minutes at least twice a day for at least 8 weeks.

16. The method of claim 14, further comprising drying the tooth after it is substantially coated in the first LC containing composition.

17. The method of claim 6, further comprising mechanically treating the tooth for at least 30 seconds at least once a day for at least one week, and wherein the mechanically treating includes one of: brushing, rubbing, scraping, or flossing.

18. A method of increasing salivary secretory Immunoglobulin A (SIgA) in a mammal comprising:
topically exposing an oral cavity to a first lithothamnium calcareum (LC) containing composition.

19. The method of claim 18, further comprising systemically exposing an oral cavity to a second LC containing composition, wherein the systemic exposure is by one of oral consumption or injection of the second LC containing composition by the mammal.

20. The method of claim 18, wherein the oral cavity is exposed to the first LC containing composition for at least 20 seconds at least once a day for at least one week, and wherein the first LC containing composition contains a solution of at least 0.01% by weight LC.

* * * * *